(12) United States Patent
Schmidt

(10) Patent No.: US 8,527,299 B2
(45) Date of Patent: Sep. 3, 2013

(54) SYSTEM AND METHOD FOR MANAGING PEDIGREE INFORMATION

(75) Inventor: Paul J. Schmidt, Brookfield, WI (US)

(73) Assignee: Accenture Global Services Limited, Dubline (IE)

( * ) Notice: Subject to any disclaimer, the term of this patent is extended or adjusted under 35 U.S.C. 154(b) by 863 days.

(21) Appl. No.: 11/610,813

(22) Filed: Dec. 14, 2006

(65) Prior Publication Data

US 2007/0143144 A1      Jun. 21, 2007

Related U.S. Application Data

(60) Provisional application No. 60/743,045, filed on Dec. 16, 2005.

(51) Int. Cl.
*G06Q 50/00* (2012.01)

(52) U.S. Cl.
USPC ...................................... 705/3; 705/2; 705/13

(58) Field of Classification Search
USPC ....................... 705/2, 3, 13; 707/9; 713/193
See application file for complete search history.

(56) References Cited

U.S. PATENT DOCUMENTS

| | | | |
|---|---|---|---|
| 6,278,999 B1 * | 8/2001 | Knapp | 707/9 |
| 6,304,849 B1 * | 10/2001 | Uecker et al. | 705/3 |
| 7,117,370 B2 * | 10/2006 | Khan et al. | 713/186 |
| 7,234,064 B2 * | 6/2007 | Menschik et al. | 713/193 |
| 2002/0077857 A1 * | 6/2002 | Seelinger | 705/2 |
| 2004/0143457 A1 * | 7/2004 | Demirian et al. | 705/2 |
| 2005/0038696 A1 * | 2/2005 | Kalevik et al. | 705/13 |
| 2005/0102173 A1 | 5/2005 | Barker et al. | |
| 2005/0137906 A1 * | 6/2005 | Kleen et al. | 705/2 |
| 2005/0187788 A1 | 8/2005 | Rivera | |
| 2005/0259818 A1 | 11/2005 | Silverbrook et al. | |
| 2005/0261935 A1 | 11/2005 | Silverbrook et al. | |
| 2006/0031094 A1 * | 2/2006 | Cohen et al. | 705/2 |

OTHER PUBLICATIONS

International Preliminary Report on Patentability mailed Jun. 26, 2008 for PCT/US2006/047751, filed Dec. 15, 2006.
PCT/US06/47751—International Search Report dated Sep. 24, 2007.

* cited by examiner

*Primary Examiner* — Valerie Lubin
(74) *Attorney, Agent, or Firm* — Mannava & Kang, P.C.

(57) ABSTRACT

Methods and systems are provided for managing and transmitting pedigree information. The methods and systems allow a user to access a pedigree information portal to submit and transmit pedigree data to a recipient of the physical drug product. The method provides security and reliability in relaying the drug history and data. In addition, methods and systems are provided for associating the electronically transmitted pedigree information to the physical drug product. A user may thus retrieve and review pedigree information using, for example, one or more barcodes representing a sender identifier and recipient identifier.

19 Claims, 6 Drawing Sheets

Drug Pedigree Information Form

Drug Information ⟵ 405

Name:
Dosage Strength:
Expiration Date:
Lot No.:
Quantity:
Invoice No.:

Drug History ⟵ 410

Source:
Date of Transaction:
Recipient:

ADD ⟵ 420    CLEAR ⟵ 425    NEW ⟵ 430

Drug History Entries
Record 1    435
Record 2

Recipient ⟵ 415
Select One...    440

SUBMIT    CANCEL    CREATE FIELD... ⟵ 445

SYSTEM AND METHOD FOR MANAGING PEDIGREE INFORMATION

FIELD OF ART

The invention relates generally to information management. More particularly, the invention provides for the formatting and transmission of product pedigree information.

BACKGROUND

The inherent dangers of prescription drugs require cautious management and recordkeeping. Current methods of managing prescription drugs include labeling drugs with a variety of information that identify and describe the drugs. Such information includes the origin of the drug product, dosage strength, expiration date, lot number, quantity and invoice number. The inclusion of such prescription drug information can provide significant safeguards against accidental or mistaken consumption or distribution.

Even with current safeguards, it is often difficult to ascertain the authenticity of the provided drug information. Thus, counterfeit drug products are able to enter the drug supply chain undetected by providing false or misleading drug information on the label. Drug counterfeiters may also falsify or alter drug delivery records to further facilitate the entry of counterfeit drugs into the supply chain. To combat this issue, many drug manufacturers and distributors are moving toward providing drug pedigree information (i.e., a documented history of a drug product's chain of custody) and associating the information with the physical product. In fact, some states have made it mandatory to include pedigree information in any acquisition, sale or trade of drug products.

However, various states or organizations that regulate such pedigree information may impose differing standards for formatting and transmitting the information. As such, a drug company must insure that the formatting of the pedigree information complies with the regulations and standards of the recipient's organization or state. In order to meet these needs, companies have implemented electronic transmission systems to facilitate the management of pedigree information. For many drug companies, however, implementing such an electronic method and/or system to comply with multiple varying standards would require a tremendous investment of resources. For example, a drug company may be required to purchase new computer equipment, acquire drug tracking components and update software in order to handle the various information format standards for the drug pedigree information. Even using paper documentation to abide by the pedigree requirements, some companies may find it difficult to keep pace with companies using electronic management solutions.

As such, methods and systems are needed for facilitating the management and transmission of drug pedigree information to enable drug companies having varying resources to comply with various information standards.

SUMMARY

The following presents a summary in order to provide a basic understanding of some aspects of the invention. The summary is not an extensive overview of the invention. It is neither intended to identify key or critical elements of the invention nor to delineate the scope of the invention. The following summary merely presents some concepts of the invention in a simplified form as a prelude to the more detailed description below.

One or more aspects comprise methods for receiving user input corresponding to drug pedigree information, determining whether a standard format is required and if so, formatting the information to comply with the standard. Additionally, a database may be maintained that stores various formatting requirements associated with different destinations (i.e., states, organizations, companies). The methods may further include authentication algorithms to securely transfer the pedigree information.

One or more additional aspects include a method for assigning a local identifier and destination identifier corresponding to user entered pedigree information and automatically generating a label with the aforementioned identifiers. For example, the label may be generated with one or more barcodes that correspond to the local identifier and/or destination identifier. Upon scanning the barcode(s), a recipient of the drug product would be able to view the pedigree information.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein:

FIG. 4 illustrates a user interface for entering and managing pedigree information according to one or more aspects described herein.

DETAILED DESCRIPTION

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope and spirit of the present invention.

Figure 1:
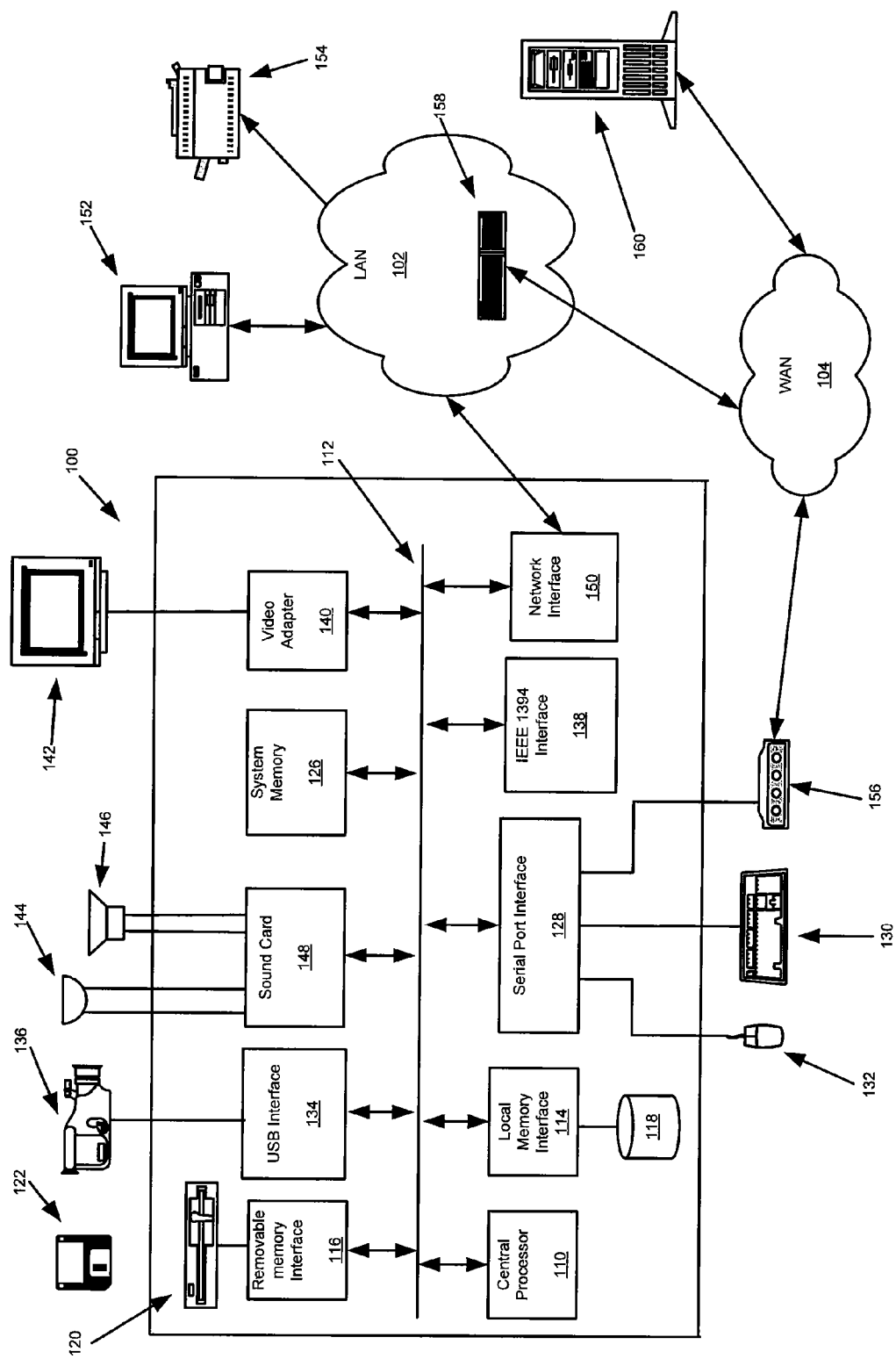
FIG. 1 is a block diagram of an illustrative operating environment in which one or more of the methods and systems of the invention may be implemented.

In order to provide solutions that enable entities to enter, manage and transmit drug product pedigree information to a recipient, the present invention is preferably implemented in conjunction with one or more computers and one or more networks. An operating environment for such a computer is illustrated in FIG. 1, in which a computer 100 is connected to a local area network (LAN) 102 and a wide area network (WAN) 104. Computer 100 includes a central processor 110 that controls the overall operation of the computer and a system bus 112 that connects central processor 110 to the components described below. System bus 112 may be implemented with any one of a variety of conventional bus architectures.

Computer 100 can include a variety of interface units and drives for reading and writing data or files. In particular, computer 100 includes a local memory interface 114 and a removable memory interface 116 respectively coupling a hard disk drive 118 and a removable memory drive 120 to system bus 112. Examples of removable memory drives include magnetic disk drives and optical disk drives. Hard disks generally include one or more read/write heads that convert bits to magnetic pulses when writing to a computer-readable medium 122 and magnetic pulses to bits when reading data from the computer readable medium 122. A single hard disk drive 118 and a single removable memory drive 120 are shown for illustration purposes only and with the understanding that computer 100 may include several of such drives. Furthermore, computer 100 may include drives for interfacing with other types of computer readable media such as magneto-optical drives.

Unlike hard disks, system memories, such as system memory 126, generally read and write data electronically and do not include read/write heads. System memory 126 may be implemented with a conventional system memory having a read only memory section that stores a basic input/output system (BIOS) and a random access memory (RAM) that stores other data and files.

A user can interact with computer 100 with a variety of input devices. FIG. 1 shows a serial port interface 128 coupling a keyboard 130 and a pointing device 132 to system bus 112. Pointing device 132 may be implemented with a hardwired or wireless mouse, track ball, pen device, or similar device.

Computer 100 may include additional interfaces for connecting peripheral devices to system bus 112. FIG. 1 shows a universal serial bus (USB) interface 134 coupling a video or digital camera 136 to system bus 112. An IEEE 1394 interface 138 may be used to couple additional devices to computer 100. Furthermore, interface 138 may configured to operate with particular manufacture interfaces such as FireWire developed by Apple Computer and i.Link developed by Sony. Peripheral devices may include touch sensitive screens, game pads scanners, printers, and other input and output devices and may be coupled to system bus 112 through parallel ports, game ports, PCI boards or any other interface used to couple peripheral devices to a computer.

Computer 100 also includes a video adapter 140 coupling a display device 142 to system bus 112. Display device 142 may include a cathode ray tube (CRT), liquid crystal display (LCD), field emission display (FED), plasma display or any other device that produces an image that is viewable by the user. Sound can be recorded and reproduced with a microphone 144 and a speaker 146. A sound card 148 may be used to couple microphone 144 and speaker 146 to system bus 112.

One skilled in the art will appreciate that the device connections shown in FIG. 1 are for illustration purposes only and that several of the peripheral devices could be coupled to system bus 112 via alternative interfaces. For example, video camera 136 could be connected to IEEE 1394 interface 138 and pointing device 132 could be connected to USB interface 134.

Computer 100 includes a network interface 150 that couples system bus 112 to LAN 102. LAN 102 may have one or more of the well-known LAN topologies and may use a variety of different protocols, such as Ethernet. Computer 100 may communicate with other computers and devices connected to LAN 102, such as computer 152 and printer 154. Computers and other devices may be connected to LAN 102 via twisted pair wires, coaxial cable, fiber optics or other media. Alternatively, radio waves may be used to connect one or more computers or devices to LAN 102.

A wide area network 104, such as the Internet, can also be accessed by computer 100. FIG. 1 shows a modem unit 156 connected to serial port interface 128 and to WAN 104. Modem unit 156 may be located within or external to computer 100 and may be any type of conventional modem, such as a cable modem or a satellite modem. LAN 102 may also be used to connect to WAN 104. FIG. 1 shows a router 158 that may connect LAN 102 to WAN 104 in a conventional manner. A server 160 is shown connected to WAN 104. Of course, numerous additional servers, computers, handheld devices, personal digital assistants, telephones and other devices may also be connected to WAN 104.

The operation of computer 100 and server 160 can be controlled by computer-executable instructions stored on a computer-readable medium. For example, computer 100 may include computer-executable instructions for transmitting information to server 160, receiving information from server 160 and displaying the received information on display device 142. Furthermore, server 160 may include computer-executable instructions for transmitting hypertext markup language (HTML) or extensible markup language (XML) computer code to computer 100.

Figure 2:
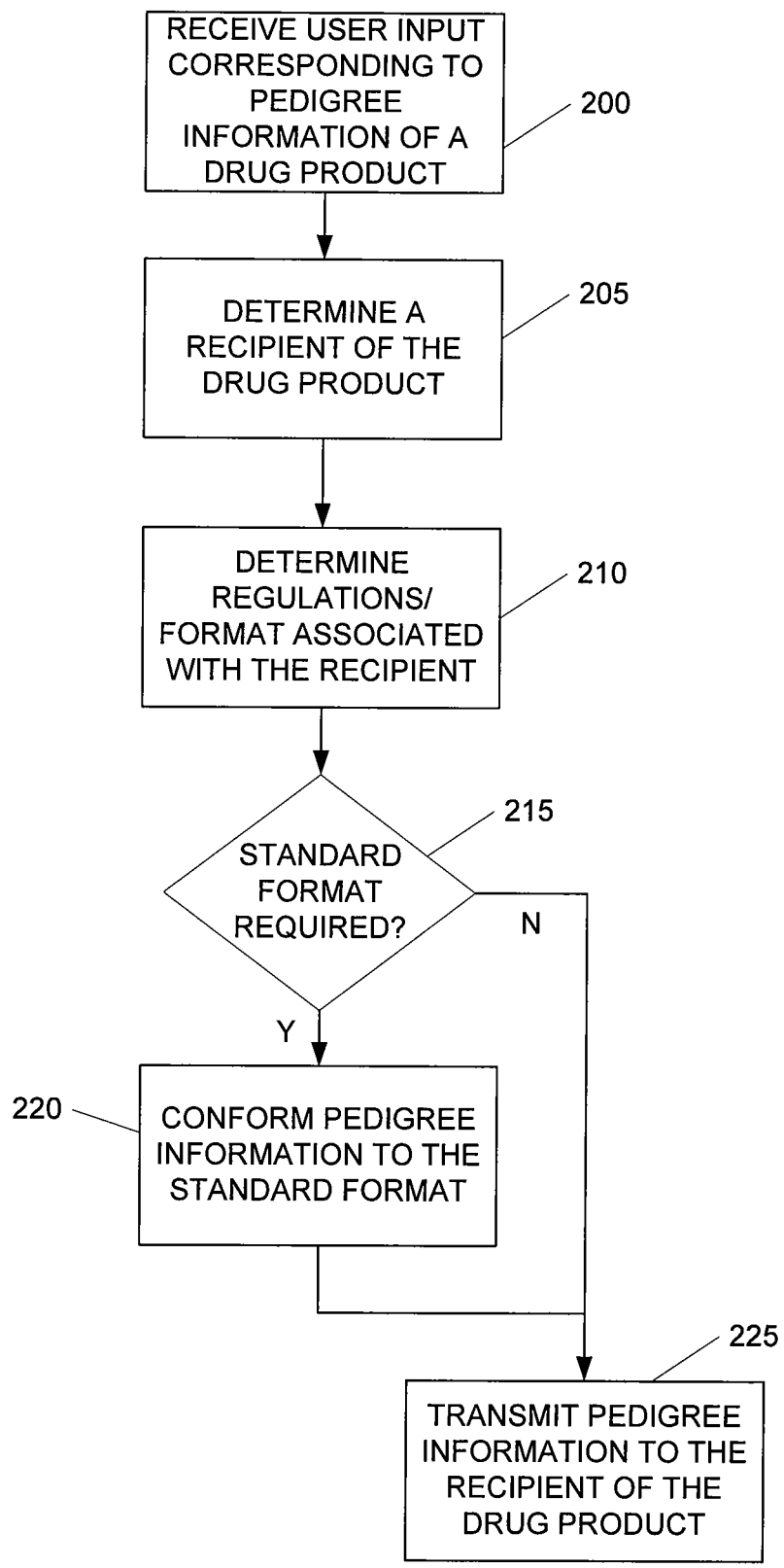
FIG. 2 is a flowchart of a method for entering, formatting and transmitting pedigree information according to one or more aspects described herein.

FIG. 2 is a flowchart illustrating a method for managing drug pedigree information. In step 200, user input relating to the drug product's pedigree information is received by a pedigree information processing system. Such information may include the sender's name or identification number, drug name/type, a lot number, and previous drug history. In addition, a user may further attach or fax files or images (e.g., drug labels) that may be relevant to the drug product. In some alternative embodiments, the user may further set limits to the transmission or access of the drug product's pedigree information. Drug companies may be sensitive to the distribution of inventory or company information and may thus wish to restrict the dissemination of pedigree data. In one example, a drug company may specify that only the specified recipient may access or view the pedigree information. In another example, a restriction may be implemented that limits the number of transmissions of the pedigree data. The user input may be entered in a variety of ways including a graphical user interface of a web page or an application. For example, a user may access a web portal interface that allows the user to enter the pedigree information for processing and transmission remotely. Such a web portal interface may be implemented using HTML code, XML programming, Active Server Pages (ASP) and the like.

Once the user has completed entry of the relevant pedigree data, one or more designated recipients of the pedigree information may then be determined from the user input in step 205. Additionally, regulations and standards for pedigree information may also be determined based on various factors associated with the designated recipient in step 210. Such factors may include location, jurisdiction and/or drug type. For example, if a recipient drug distributor operates in Florida, the pedigree information requirements and standards for Florida would be selected or identified. In some embodiments, the pedigree information requirements and regulations for numerous jurisdictions may be stored in a local database and updated periodically or whenever needed. In such instances, a system implementing the methods described herein may locate and extract the rules and regulation data from the local database based on the recipient data entered by the user. Alternatively, a system may consult a third party server or database. If such rules and regulations exist, a further determination may be made in step 215 as to whether the rules and regulations are required. If the standards are required, the pedigree data may be formatted or packaged to insure compliance with the regulations in step 220. In one example, the pedigree data may be formatted using XML coding and transmission techniques. The formatted pedigree data may then transmitted to the recipient in step 225. If, however, a standard format exists but is not required (i.e., not enforced), the pedigree data may be sent without pre-formatting. A decision as to whether to format the data or not may be made by a manual determination or a default system setting.

In one or more alternative embodiments, the recipient of the drug pedigree information may also evaluate the information to determine compliance with the proper regulations and standards. If the information format is non-compliant, the recipient may issue an error or rejection message to the sender through the pedigree information system identifying the errors in formatting. The pedigree information system may then automatically reformat the pedigree data according to the instructions contained in the error message. Alternatively or additionally, the sender may modify the entered data manually to compensate for the identified errors.

The transmissions described in the method of FIG. 2 may use any of a multitude of network types. In addition, the transmissions may be encoded or otherwise authenticated in order to guarantee security and authenticity of received data. For example, the data transmission may be sent via one or more trusted agents that act as intermediaries to guarantee the sender's identity as well as the recipient's identity. The trusted agents may receive certificates from a granting authority not subject to influence from an outside source. Alternatively, transmissions may be encrypted using techniques such as RSA key pairs (i.e., public and private keys) to prevent interception or unauthorized access of the data. Another method for authenticating and securing transmission is through the use of digital signatures. For example, a processing system may implement an XML based digital signature algorithm for handling authentication of transmissions.

Figure 3:
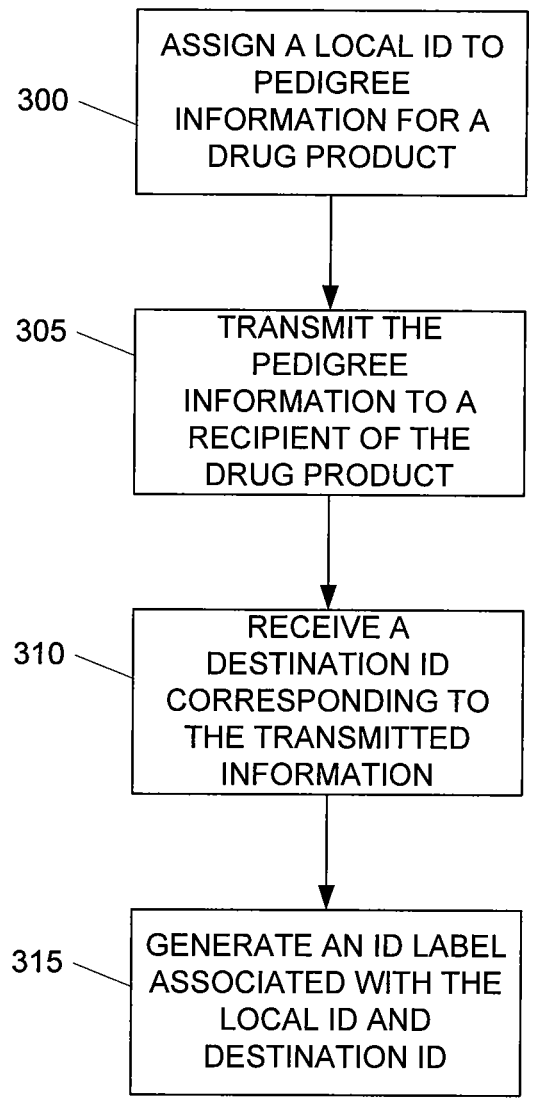
FIG. 3 is a flowchart illustrating a method for associating electronically transmitted pedigree information with a physical drug product according to one or more aspects described herein.

To further protect the integrity of pedigree information, an association may be created between the electronically transmitted information and the physical drug product. FIG. 3 illustrates a method for associating electronic pedigree data with the physical drug product. In step 300, a local (i.e., sender) identifier may be assigned to the pedigree information of a drug product. Such an identifier may include an identification number, a graphical symbol, an alphanumeric code and the like. The sender identifier represents an association between the physical drug product and the pedigree information stored on the sending system. After an identifier has been assigned to the pedigree information, the information may then be transmitted to the recipient in step 305 using methods similar to the ones described in FIG. 2. Upon receipt of the pedigree data, a confirmation to the sender along with a recipient or destination identifier associated with the pedigree information may be received in step 310. A label may then be generated for the physical drug product containing the local identifier or the destination identifier or both in step 315. In one alternative, the local identifier and/or the destination identifier may be represented using barcodes to allow a recipient of the physical product to scan the barcode and retrieve the pedigree information. The label may be attached to the drug product so that pedigree information may be retrieved or otherwise located using the sender and/or recipient identifier.

FIG. 4 illustrates a graphical user interface, i.e., interface 400, for entering and submitting pedigree information. As described previously, graphical user interface 400 may be implemented in a variety of ways including web-based implementations as well as application-based implementations. The interface 400 may include several data sections including Drug Information 405, Drug History 410 and Recipient 415. Drug Information portion 405 of interface 400 allows a user to enter information and characteristics of the drug, itself. For example, a user may enter a drug name, dosage strength, expiration date, lot number, quantity and/or invoice number. In Drug History section 410, a user may provide the transaction history of the drug product including the source, the date of transaction and the recipient. Once the data has been entered, the user may select ADD option 420 to create the record. Additional records may be added using NEW option 430. Alternatively, if the user entered incorrect data, he or she may use CLEAR option 425 to clear the current entries. Furthermore, Drug History Entries list 435 permits a user to review previously entered records and either edit or delete them.

The Recipient field 415 may include drop down menu 440 allowing a user to select a recipient from a predefined list. Alternatively, Recipient field 415 may provide a text entry field (not shown) that permits a user to manually specify the name of the recipient. A processing system may then search for matches in a database in order to identify the designated recipient. Depending on the standards of the recipient's jurisdiction, one or more of these fields may be required for proper submission. In one or more embodiments, user interface 400 may further provide a user with a menu of pedigree information formats (not shown), allowing the user to manually select the submission/transmission standard and override any automatic selections.

Alternatively or additionally, interface 400 may include create field option 445 that allows a user to define his or her own data entry field. Accordingly, if a user wishes to enter a type of information for which a field is not provided, the user may select option 445 to name the new field and enter the data associated with that new field. In one or more configurations, selection option 445 may open a new dialogue window or interface. In one example, a user may wish to create an instructions field for entering specific instructions for taking a particular medication. The user may select option 445 to create an instructions field and enter the corresponding information.

Figure 5:
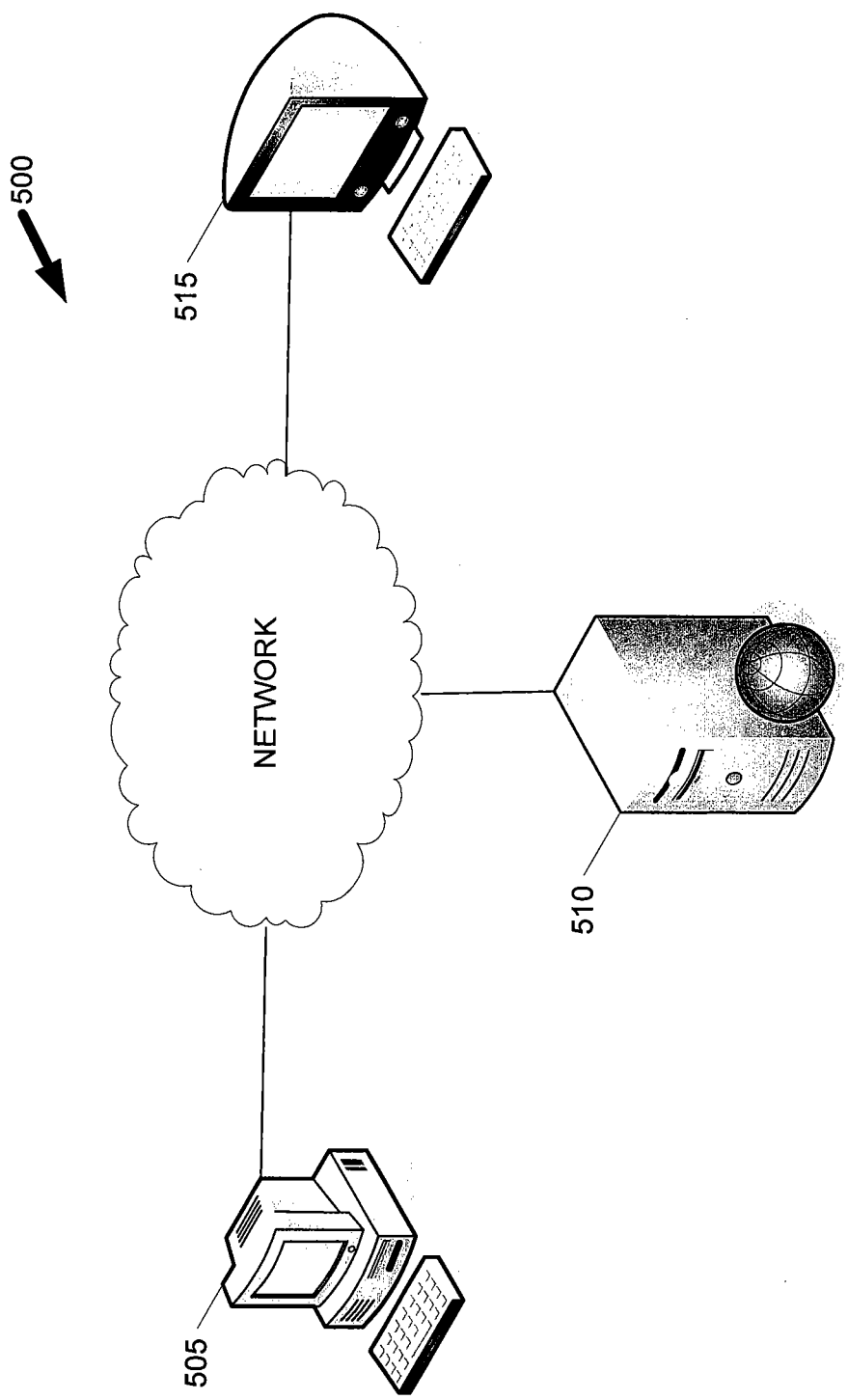
FIG. 5 illustrates a diagram of a network through which product pedigree information may be transmitted according to one or more aspects described herein.

FIG. 5 illustrates a diagram of a networked system for distributing drug pedigree information in which various aspects described herein may be implemented. Network system 500 may include entities such as drug source system 505, pedigree information system 510 and drug recipient system 515. Systems 505, 510 and 515 may be connected through a variety of types of networks such as the Internet. In addition, the networks may be established using a variety of protocols that provide either wired or wireless connections or both. For example, system 505 may be connected to pedigree information system 510 over a wireless local area network (WLAN) connection. Systems 505, 510 and 515 may comprise various types of devices including personal data assistants (PDA), personal computers (PC), network server systems, mobile communication devices (e.g., cell phones) and/or combinations thereof. Additionally, network system 500 may include one or more routing devices or systems situated between systems 505, 510 and 515 to aid in directing and/or filtering data.

In one or more configurations, a drug wholesaler who might not have its own internal drug pedigree information system may access remote pedigree information system 510 over a network through local system 505. The drug wholesaler may thus use the pedigree information applications and functionality provided by system 510 to provide drug pedigree data in an appropriate fashion. For example, if drug wholesaler has sold a particular drug to a recipient corresponding to system 515, the drug wholesaler may use system 510 to format and transmit the drug pedigree information associated with the sold drugs. In one or more instances, system 510 may determine regulations and requirements associated with the drug sale transaction and prepare drug pedigree information received from a drug wholesaler in accordance with those regulations and requirements. Once the drug pedigree information has been prepared, the information may then be transmitted to a recipient system associated with the drug purchaser like system 515.

Figure 6:
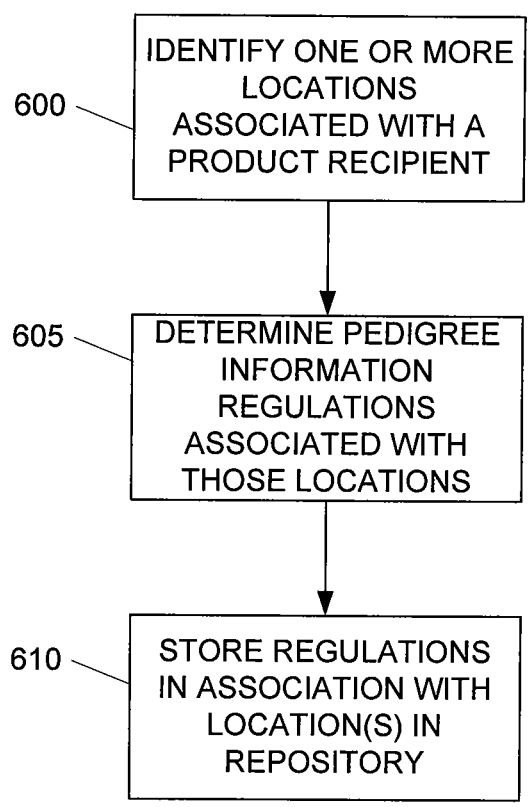
FIG. 6 is a flowchart illustrating a method for determining pedigree information regulations and storing those regulations in association with one or more attributes according to one or more aspects described herein.

FIG. 6 is a flowchart illustrating a method for determining pedigree information regulations and storing those regulations in a repository. In step 600, for example, a pedigree information system may identify a location or locations associated with a product recipient. The product recipient may be preprogrammed or predefined in the information system. Locations may be determined based on zipcodes, street addresses, phone numbers and other information. Once a location has been identified, pedigree information regulations may be determined based on the location in step 605. Regulations may be manually entered by a user or may be obtained electronically by querying a database corresponding to the location. In one example, a state government may maintain a database of forms and/or regulations associated with product pedigree information. As such, upon determining the location, a pedigree information system may access the database corresponding to the location (e.g., state) and obtain the relevant forms and regulations. In step 610, the pedigree information system may then store the regulations and/or forms in association with the location in a repository. Thus, when regulations need to be identified, the pedigree information system may query the repository using the location of a specified recipient.

Alternatively or additionally, pedigree information regulations may be identified and stored in association with one or more other characteristics or attributes. For example, regulations may depend on a type of product or a type of organization. If an organization is a for profit company, the pedigree information requirements may be different than for a non-profit organization. Similarly, regulations may be different for pedigree information associated with drug products than for firearms. As such, in one or more arrangements, regulation information may be stored in association with a combination of attributes and characteristics.

While the above methods and systems have been described with respect to drug products and drug pedigree information, the methods and systems may also be used in other industries and for other products. For example, the firearm industry may also benefit from a pedigree information system in order to track firearm possession and safeguard against illegal weapons or possession of weapons. Additionally, pedigree information may provide a potential purchaser with data regarding criminal records associated with the firearm. Other products to which a pedigree system may be applied include tobacco products, alcoholic products and the like.

Additionally, the methods and features recited herein may further be implemented through any number of computer readable mediums that are able to store computer readable instructions. Examples of computer readable media that may be used include RAM, ROM, EEPROM, flash memory or other memory technology, CD-ROM, DVD or other optical disk storage, magnetic cassettes, magnetic tape, magnetic storage and the like.

The present subject matter has been described in terms of preferred and exemplary embodiments thereof. It is to be understood that the subject matter defined in the appended claims is not necessarily limited to the specific features or acts described above. Rather, the specific features and acts described above are disclosed as example forms of implementing the claims.

I claim:

1. A method for managing product pedigree information, the method comprising:
   receiving pedigree information corresponding to a product;
   determining a recipient of the product including a location of the recipient;
   determining one or more product regulations based on the location of the recipient;
   determining that the one or more product regulations require a pedigree information format;
   formatting, by a processor, the received pedigree information in accordance with the format;
   generating a code representing a recipient identifier of the recipient and a sender identifier, wherein the code is associated with the product;
   retrieving the pedigree information by using the code;
   electronically transmitting the formatted pedigree information to the recipient over a network in response to receiving a communication comprising the code;
   receiving, by the processor, an error message including instructions from the recipient, the error message identifying an error in formatting; and
   automatically reformatting, by the processor, the pedigree information according to the instructions included within the error message.

2. The method of claim 1, wherein the product is a pharmaceutical drug product.

3. The method of claim 2, wherein the pedigree information includes at least one of: source identification information, dosage information, chain of ownership data, and expiration date information.

4. The method of claim 1, wherein the pedigree information is received over the network from a remote source not having an internal pedigree information system.

5. The method of claim 4, wherein the recipient includes the internal pedigree information system.

6. The method of claim 1, further comprising assigning a source identification number to the pedigree information of the product.

7. The method of claim 6, further comprising:
   associating the recipient identifier with the pedigree information; and
   storing the source identification number in association with the recipient identifier.

8. A non-transitory computer readable medium to store computer executable instructions that, when executed, cause a processor to:
   receive pedigree information corresponding to a product;
   determine a recipient of the product including a location of the recipient;
   determine one or more product regulations based on the location of the recipient;
   determine that the one or more product regulations require a pedigree information format;
   format the received pedigree information in accordance with the pedigree information format;
   generate a code representing a recipient identifier of the recipient and a sender identifier, wherein the code is associated with the product;

retrieve the pedigree information by using the code;

electronically transmit the formatted pedigree information to the recipient over a network in response to receiving a communication comprising the code;

receive an error message including instructions from the recipient, the error message identifying an error in formatting; and automatically reformat the pedigree information according to the instructions included within the error message.

9. The non-transitory computer readable medium of claim 8, wherein the product is a pharmaceutical drug product.

10. The non-transitory computer readable medium of claim 9, wherein the pedigree information includes at least one of: source identification information, dosage information, chain of ownership data, and expiration date information.

11. The non-transitory computer readable medium of claim 8, wherein the pedigree information is received over the network from a remote source not having an internal pedigree information system.

12. The non-transitory computer readable medium of claim 8, wherein the computer executable instructions are to assign a source identification number to the pedigree information of the product.

13. The non-transitory computer readable medium of claim 12, wherein the computer executable instructions are to:

associate the recipient identifier with the pedigree information; and store the source identification number in association with the recipient identifier.

14. An apparatus comprising:

a processor; and a memory to store computer executable instructions that, when executed by the processor, cause the apparatus to:

receive pedigree information corresponding to a product;

determine a recipient of the product including a location of the recipient;

determine one or more product regulations based on the location of the recipient;

determine that the one or more product regulations require a pedigree information format;

format the received pedigree information in accordance with the format;

generate a code representing a recipient identifier of the recipient and a sender identifier, wherein the code is associated with the product;

retrieve the pedigree information by using the code;

electronically transmit the formatted pedigree information to the recipient over a network in response to receiving a communication comprising the code;

receive an error message including instructions from the recipient, the error message identifying an error in formatting; and automatically reformat the pedigree information according to the instructions included within the error message.

15. The apparatus of claim 14, wherein the computer executable instructions cause the apparatus to assign a source identification number to the pedigree information of the product.

16. The apparatus of claim 15, wherein the computer executable instructions cause the apparatus to:

associate the recipient identifier with the pedigree information; and store the source identification number in association with the recipient identifier.

17. The method of claim 1, further comprising determining that the formatted pedigree information has been transmitted less than a predetermined number of times prior to the electronic transmission of the formatted pedigree information to the recipient.

18. The method of claim 1, further comprising verifying an identity of the recipient prior to the electronic transmission of the formatted pedigree information to the recipient.

19. The method of claim 1, further comprising generating an extensible markup language based digital signature for authentication of the electronic transmission.

* * * * *